(12) United States Patent
Kato et al.

(10) Patent No.: US 10,322,278 B2
(45) Date of Patent: Jun. 18, 2019

(54) CLAMPING DEVICE

(71) Applicant: Nikkiso Company Limited, Tokyo (JP)

(72) Inventors: Ryo Kato, Shizuoka (JP); Shigeaki Funamura, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 15/844,764

(22) Filed: Dec. 18, 2017

(65) Prior Publication Data

US 2018/0104467 A1 Apr. 19, 2018

Related U.S. Application Data

(63) Continuation of application No. PCT/JP2016/068210, filed on Jun. 20, 2016.

(30) Foreign Application Priority Data

Jun. 22, 2015 (JP) .................................. 2015-124399

(51) Int. Cl.
*F16K 7/04* (2006.01)
*A61M 39/28* (2006.01)

(52) U.S. Cl.
CPC .......... *A61M 39/28* (2013.01); *A61M 39/284* (2013.01)

(58) Field of Classification Search
CPC ........ F16K 7/066; F16K 7/065; A61M 39/28; A61M 39/284

(Continued)

(56) References Cited

U.S. PATENT DOCUMENTS 350,850 A 10/1886 Tatum
3,419,245 A 12/1968 Scola
(Continued)

FOREIGN PATENT DOCUMENTS

EP 0637456 A1 2/1995
EP 0691139 A1 1/1996
(Continued)

OTHER PUBLICATIONS

International Search Report from the Japanese Patent Office for Application No. PCT/JP2016/068210 dated Aug. 2, 2016.

(Continued)

*Primary Examiner* — Umashankar Venkatesan
(74) *Attorney, Agent, or Firm* — The Dobrusin Law Firm, PC

(57) ABSTRACT

A clamping device is provided in which an other end portion is prevented from being excessively displaced in the transition from a clamped state to an unclamped state. A clamping device includes a one end portion having a locked part at a tip, an other end portion having a locking part capable of locking the locked part, a middle portion continuous with the one end portion and with the other end portion, and an insertion hole (H1, H2) allowing a flexible tube T to be inserted therethrough. An unclamped state is established when the locked part locked is unlocked by bending the other end portion such that the other end portion is displaced from the one end portion. The clamping device is configured to clamp the flexible tube T in a clamped state where a first projection and a second projection are positioned close to each other and to intercept a flow of a fluid at a clamped position. The clamping device further includes displacement-restricting members capable of restricting the displacement of the other end portion in a transition from the clamped state to the unclamped state.

5 Claims, 7 Drawing Sheets

(58) Field of Classification Search
USPC .................................................. 251/9, 10
See application file for complete search history.

(56) References Cited

U.S. PATENT DOCUMENTS

| | | | |
|---|---|---|---|
| 3,698,681 | A | 10/1972 | Lacey |
| 3,822,052 | A | 7/1974 | Lange |
| 4,053,135 | A | 10/1977 | Saliaris |
| 4,235,412 | A | 11/1980 | Roth et al. |
| 4,589,626 | A * | 5/1986 | Kurtz ............... A61M 39/288 251/10 |
| 4,643,389 | A | 2/1987 | Elson et al. |
| 5,035,399 | A * | 7/1991 | Rantanen-Lee ...... A61M 39/28 251/10 |
| 5,083,741 | A | 1/1992 | Sancoff |
| 5,203,056 | A | 4/1993 | Funk et al. |
| 5,238,218 | A | 8/1993 | Mackal |
| 6,089,527 | A * | 7/2000 | Utterberg ........... A61M 39/284 251/4 |
| 6,113,062 | A * | 9/2000 | Schnell ............. A61M 39/284 251/10 |
| 6,592,558 | B2 | 7/2003 | Quah |
| 6,698,681 | B1 | 3/2004 | Guy et al. |
| 8,469,331 | B2 * | 6/2013 | Burbank ............. A61M 1/1656 251/4 |
| 8,474,784 | B2 | 7/2013 | Kashmirian et al. |
| 9,829,113 | B2 * | 11/2017 | Brugger ............ B29C 37/0003 |
| 2004/0089828 | A1 | 5/2004 | Werth |
| 2007/0261214 | A1 | 11/2007 | Nerbonne |
| 2010/0152681 | A1 | 6/2010 | Mathias |
| 2010/0268161 | A1 | 10/2010 | Traversaz |
| 2012/0232497 | A1 | 9/2012 | Singh |
| 2013/0310768 | A1 * | 11/2013 | Ebara ................. A61M 5/168 604/250 |
| 2014/0074047 | A1 | 3/2014 | Calderon |
| 2014/0336613 | A1 | 11/2014 | Roth et al. |

FOREIGN PATENT DOCUMENTS

| | | |
|---|---|---|
| EP | 2332611 A1 | 12/2009 |
| JP | S62-053667 A | 3/1987 |
| JP | H05-023792 B2 | 4/1993 |
| JP | 2001-353215 A | 12/2001 |
| JP | 2002-210006 A | 7/2002 |
| JP | 2003-235971 | 8/2003 |
| JP | 2005-027721 A | 2/2005 |
| JP | 2009-022744 | 2/2009 |
| JP | 2012-075520 | 4/2012 |
| JP | 4922246 B2 | 4/2012 |
| JP | 2013-176543 A | 9/2013 |
| JP | 2014-530076 A | 11/2014 |
| WO | 2012/111310 A1 | 8/2012 |
| WO | 2014/162376 | 9/2014 |

OTHER PUBLICATIONS

Co-Pending U.S. Appl. No. 15/392,748, filed Dec. 28, 2016.
Co-Pending U.S. Appl. No. 15/665,635, filed Aug. 1, 2017.
Extended European Search Report dated Jan. 18, 2019, Application No. 16814295.8.

* cited by examiner

[Fig. 1]
(a)
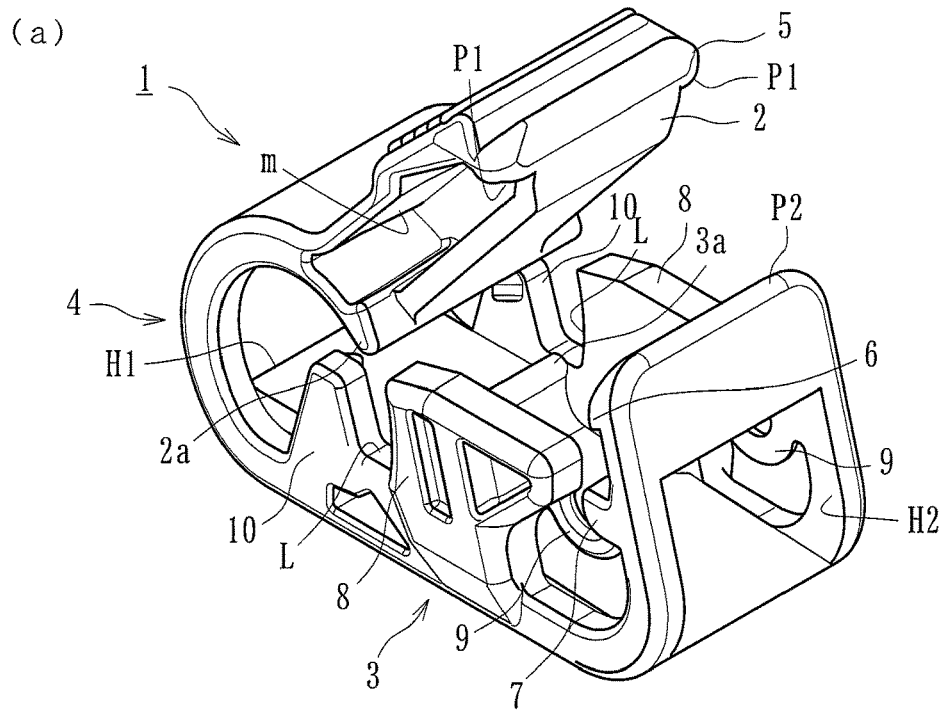
(b)
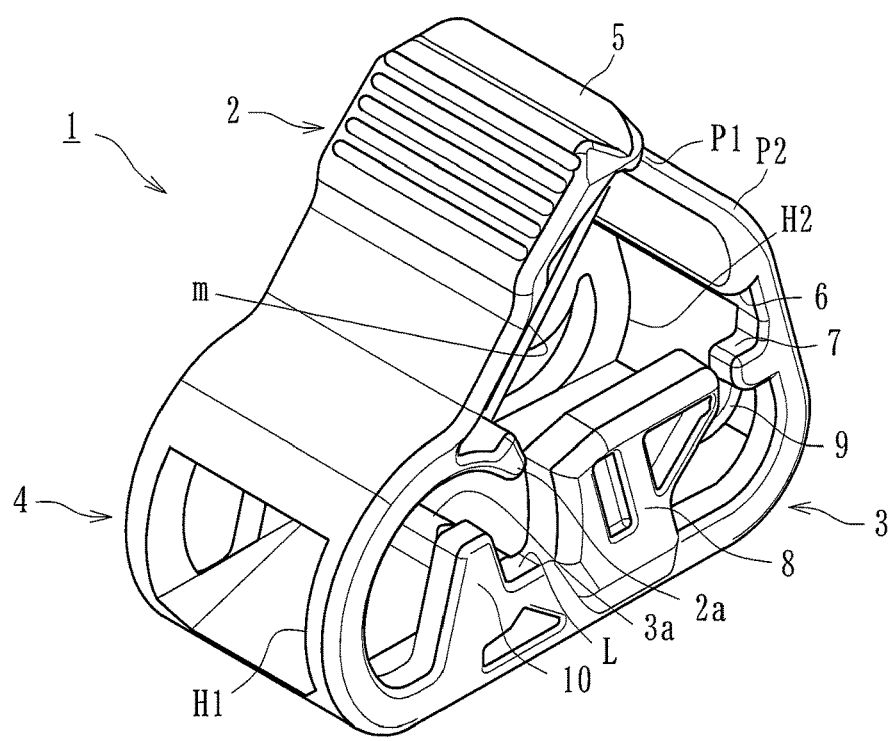

[Fig. 2]
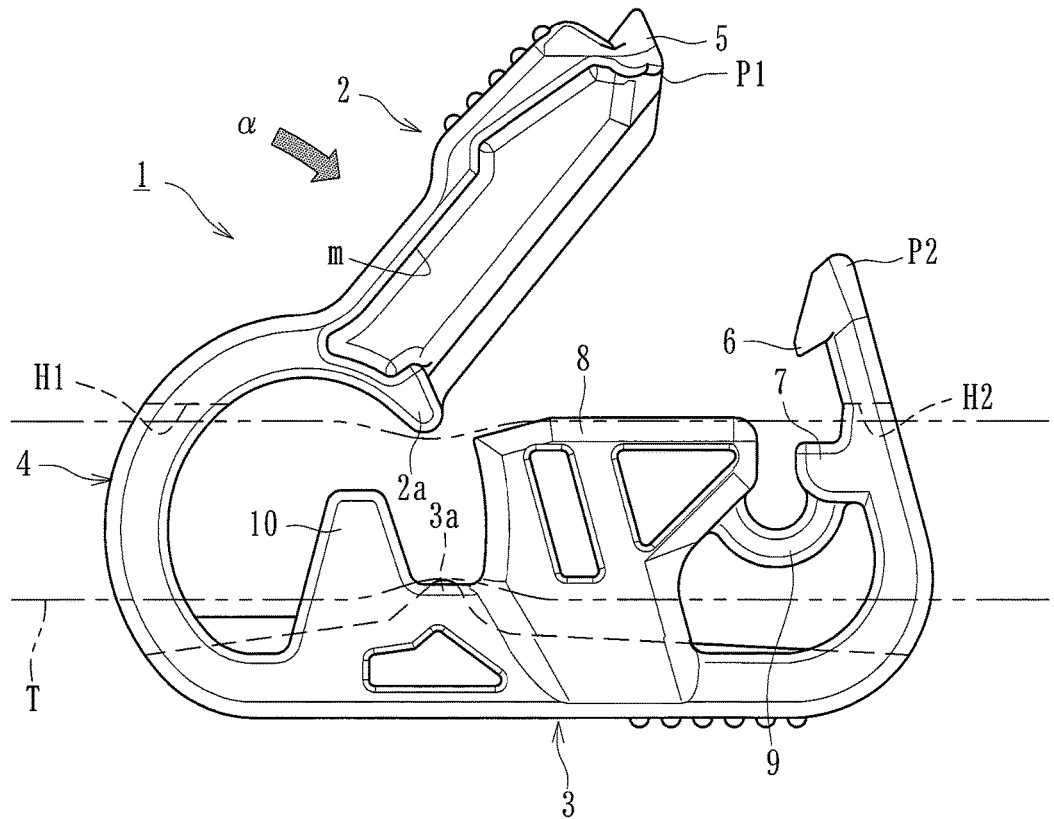
[Fig. 3]
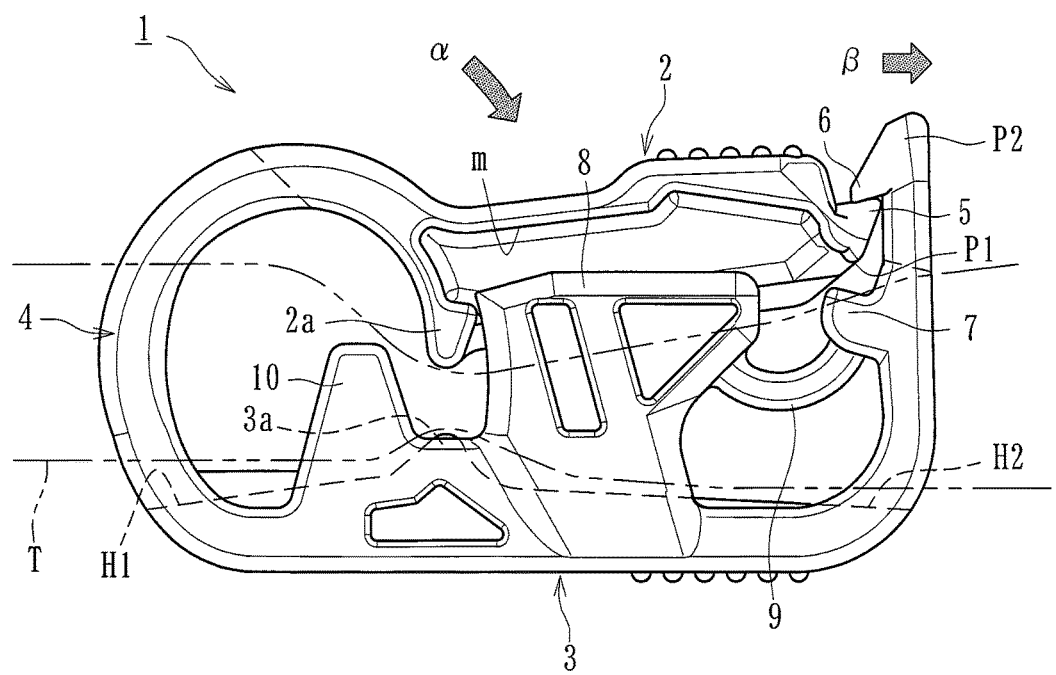

[ Fig. 4 ]
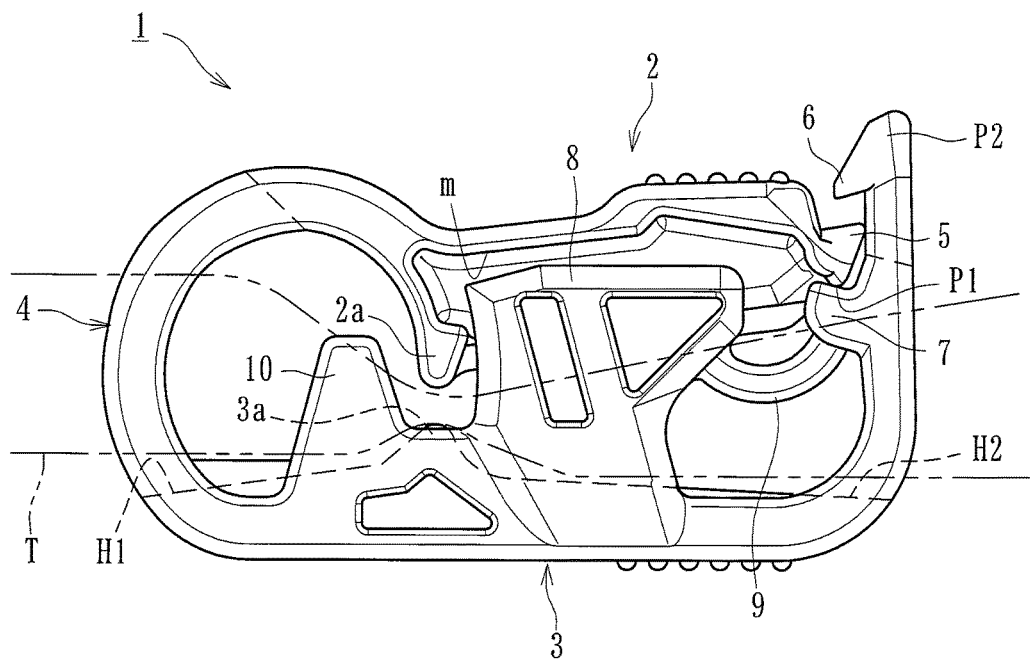
[ Fig. 5 ]
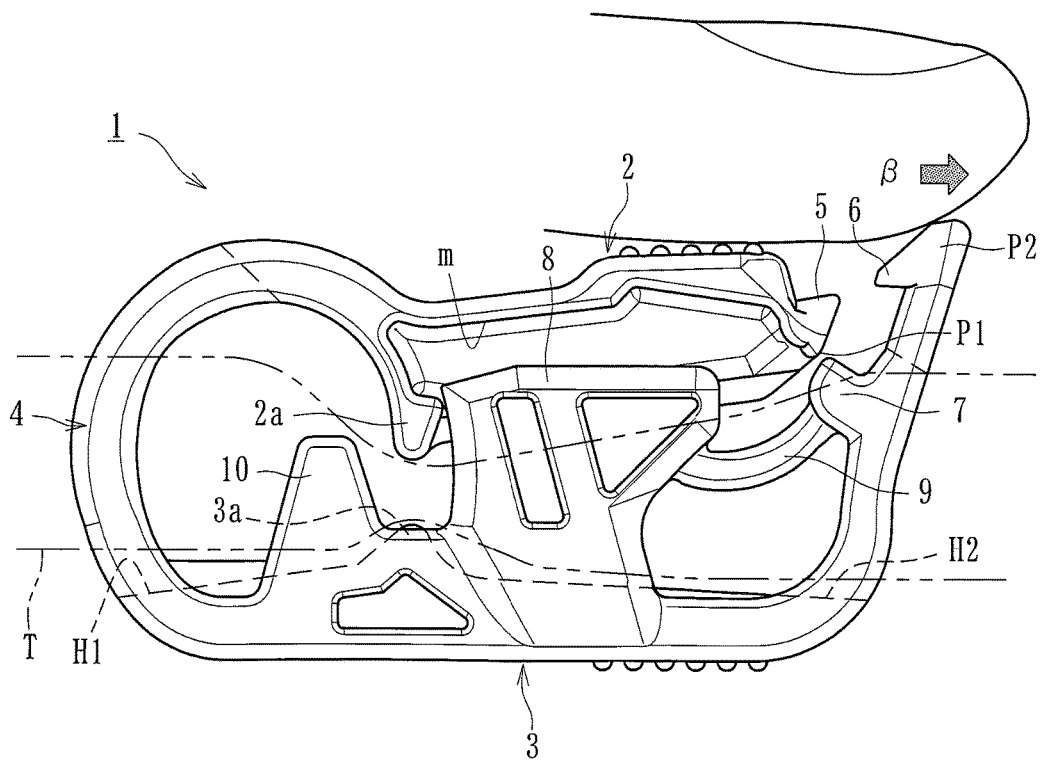

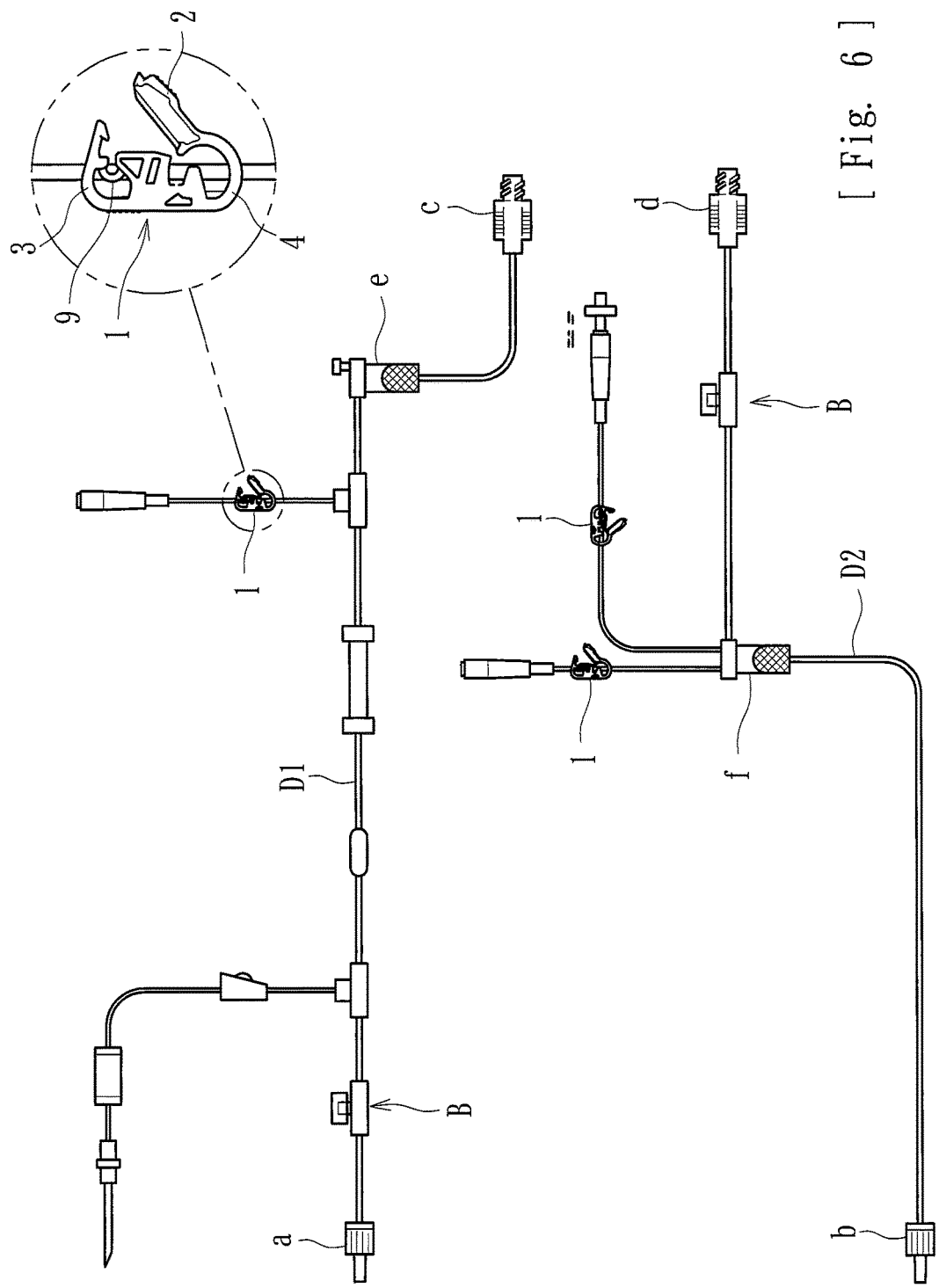
[Fig. 6]

[Fig. 7]
(a)
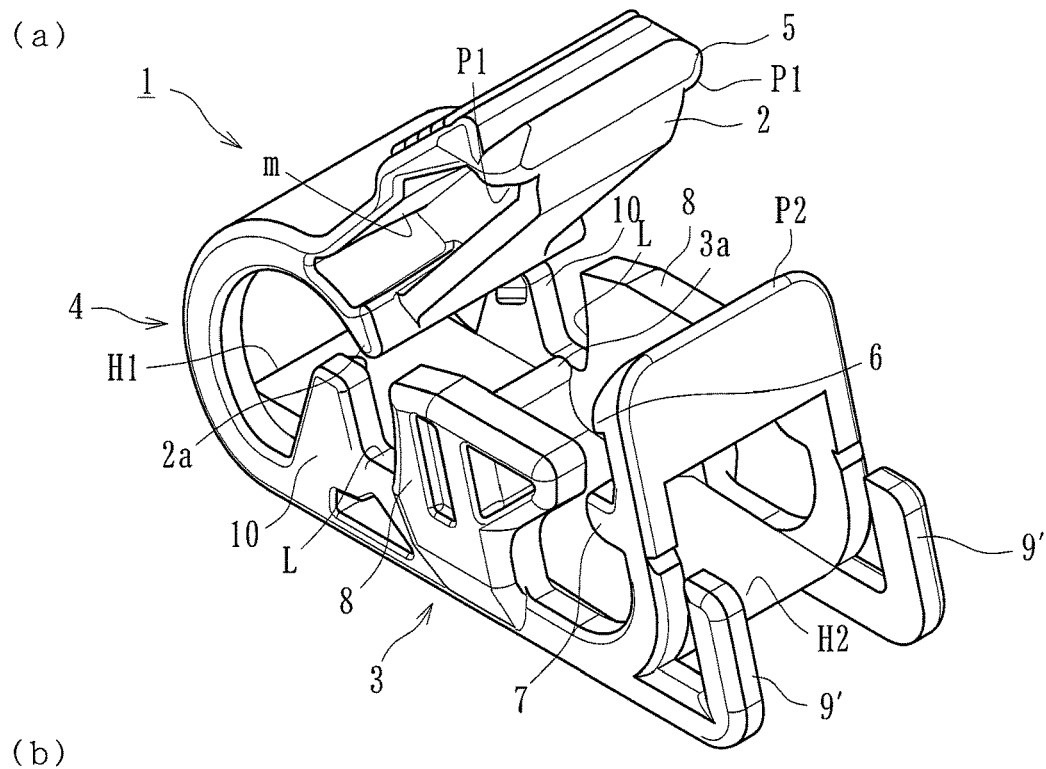
(b)
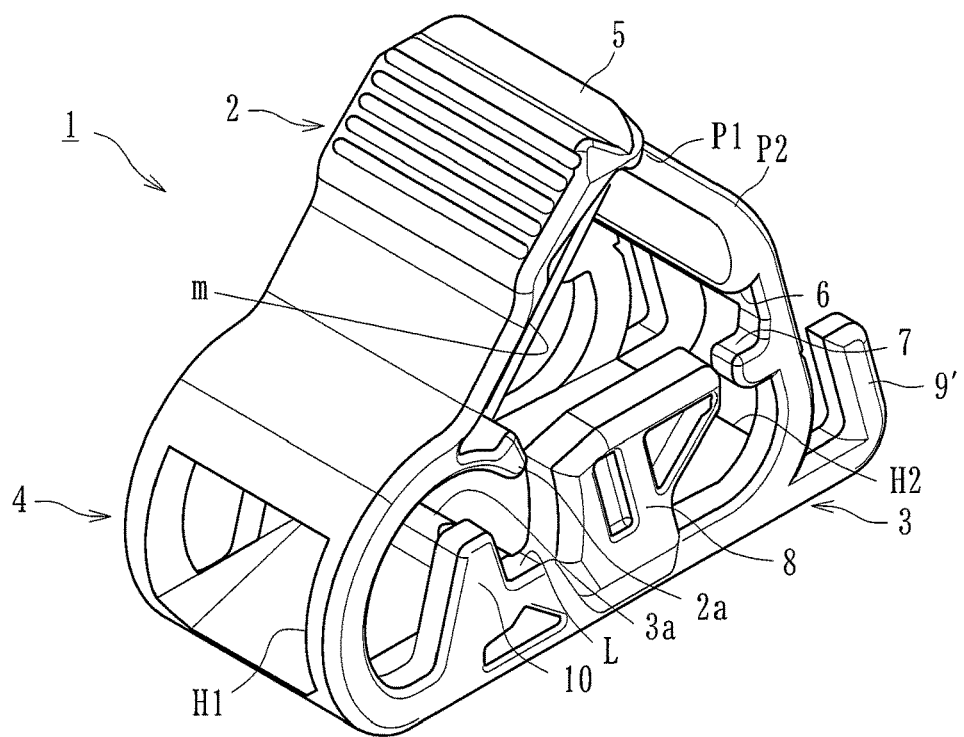

[ Fig. 8 ]
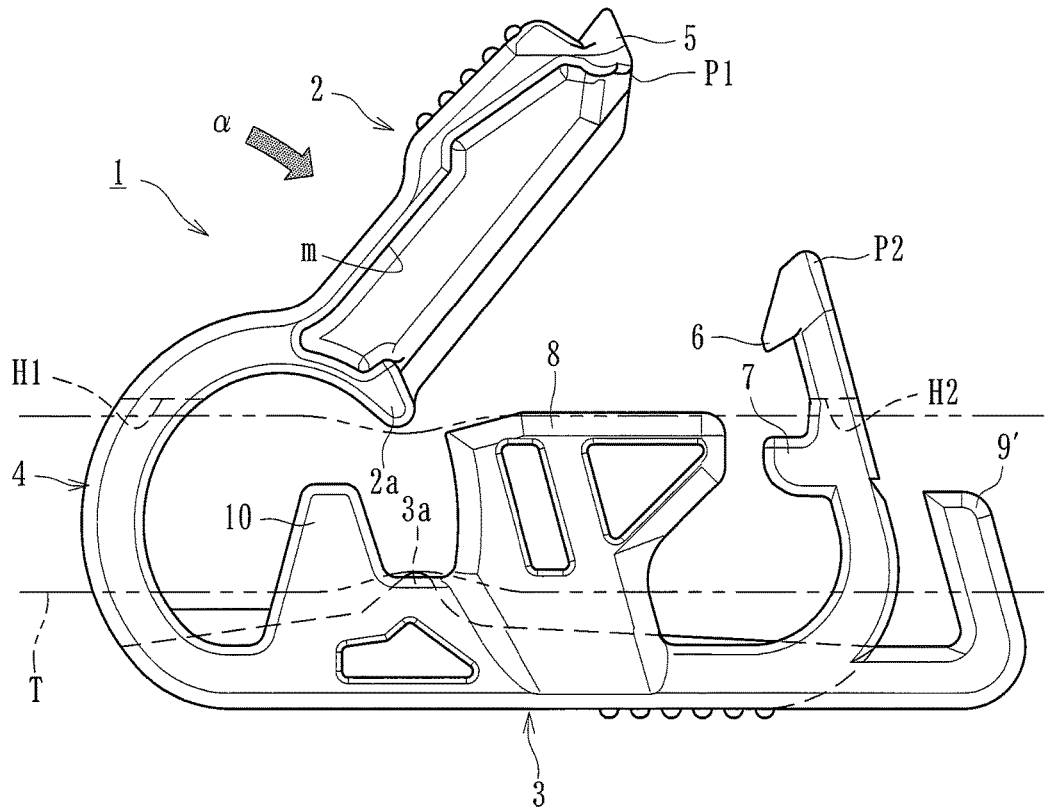
[ Fig. 9 ]
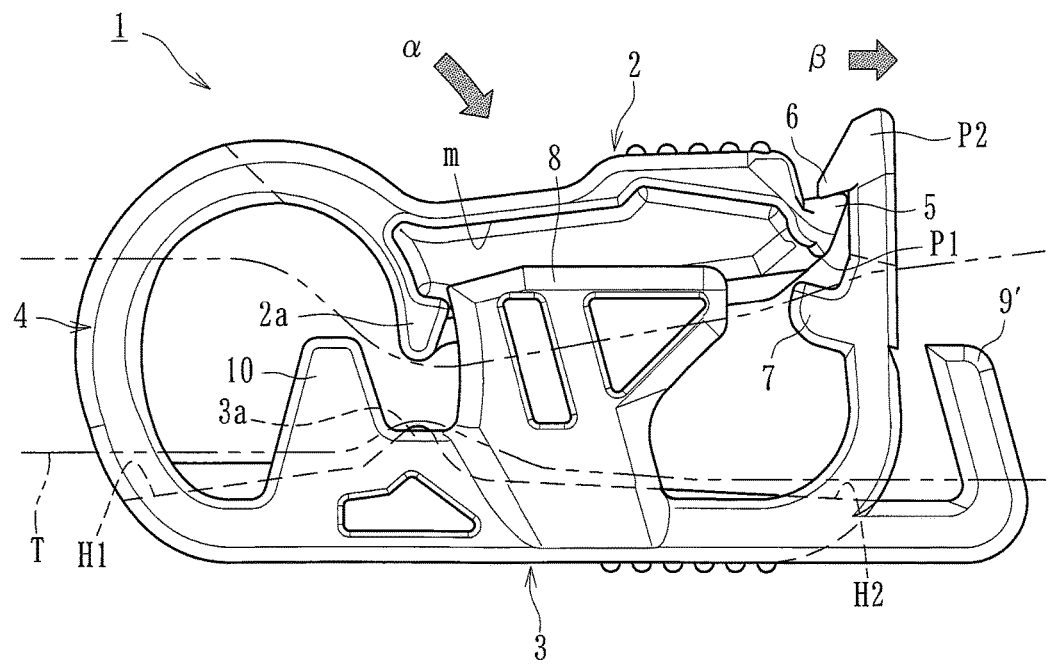

[ Fig. 10 ]
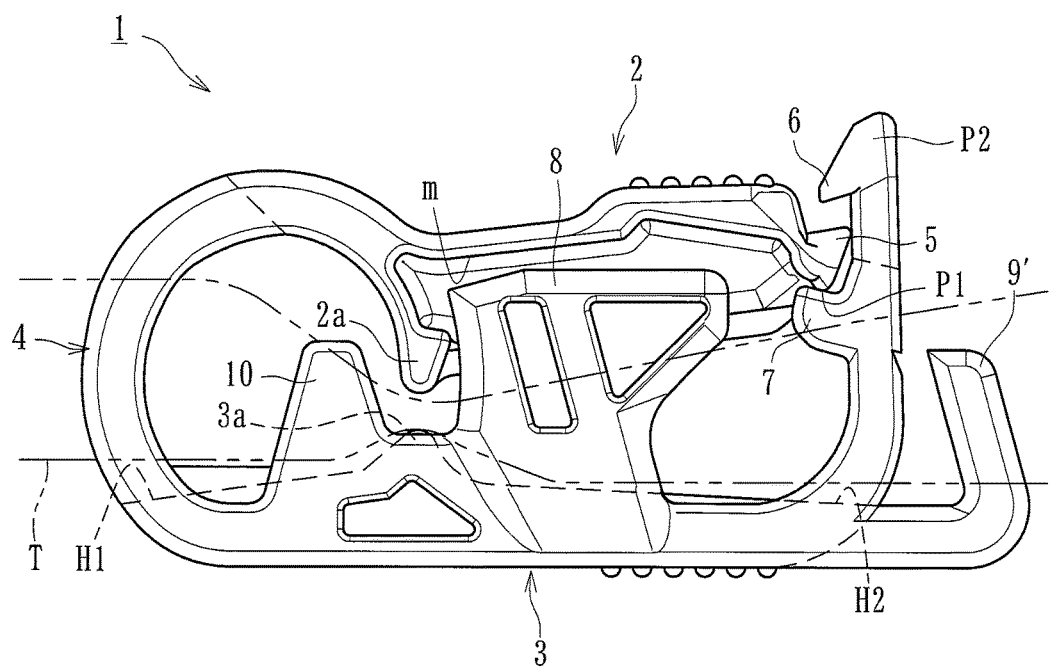
[ Fig. 11 ]
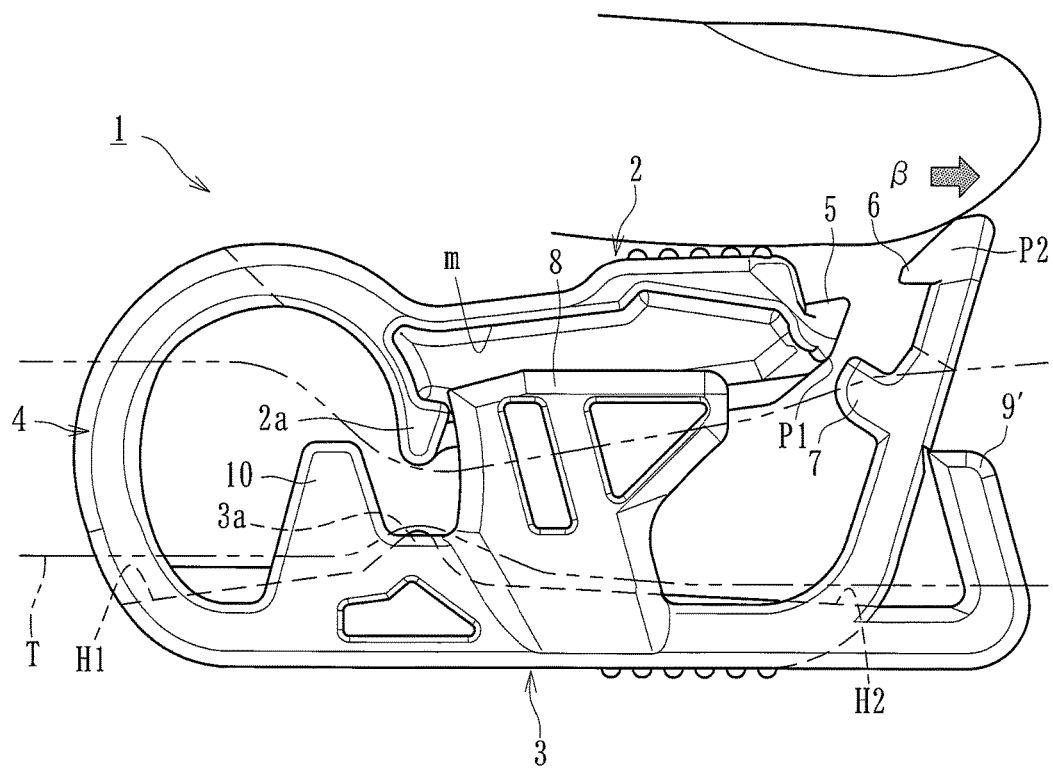

CLAMPING DEVICE

FIELD

The present teachings relate to a clamping device that clamps a flexible tube and intercepts the flow of a fluid at the clamped position.

BACKGROUND

In general, a blood circuit included in a dialysis apparatus or the like basically includes a flexible tube that allows a fluid, such as the blood of a patient, a physiological saline solution, or a drug to be given, used in a medical site to flow therethrough and connects various elements such as a dialyzer and an air-trap chamber to one another. A hitherto known clamping device for arbitrarily intercepting a desired position of such a flexible tube includes a one end portion having a first projection on the inner side thereof and a locked part at the tip thereof, an other end portion having a second projection at a position thereof facing the first projection and also having a locking part capable of locking the locked part, a middle portion continuous with the one end portion and with the other end portion, and an insertion hole allowing a flexible tube to be inserted between the first projection and the second projection (see PTL 1, for example).

When the one end portion is pressed and is brought closer to the other end portion, the locking part locks the locked part, whereby a clamped state is established. Furthermore, when the other end portion is bent in such a manner as to be displaced from the one end portion, the locked part locked by the locking part can be unlocked, whereby an unclamped state is established. In the clamped state, the first projection and the second projection are positioned close to each other and thus clamp the flexible tube. Accordingly, the flow of the fluid (liquid such as blood, a physiological saline solution, or the like; or gas such as air) can be intercepted arbitrarily at the clamped position.

CITATION LIST

PTL 1: Japanese Unexamined Patent Application Publication No. 2013-176543 the teachings of which are incorporated by reference herein for all purposes.

SUMMARY

In the above known device, however, the other end portion is unlimitedly displaceable in the direction in which the state of the device is changed from the clamped state to the unclamped state. Therefore, in the transition from the clamped state to the unclamped state, the other end portion may be bent excessively and be displaced excessively. In such a case, the other end portion may be plastically deformed. If the other end portion is plastically deformed, the clamped state cannot be established any more, or the engaging part might not completely engage with the engaged part even in the clamped state. Such a situation leads to a problem that the interception of the flow of the fluid is incomplete.

The present teachings have been conceived in view of the above circumstances and provides a clamping device in which an other end portion is prevented from being excessively displaced in the transition from a clamped state to an unclamped state.

According to the teachings herein, there is provided a clamping device including a one end portion having a first projection on an inner side and a locked part at a tip, an other end portion having a second projection at a position facing the first projection and a locking part capable of locking the locked part, a middle portion continuous with the one end portion and with the other end portion, and an insertion hole allowing a flexible tube to be inserted between the first projection and the second projection. A clamped state where the locked part is locked by the locking part is established when the one end portion is pressed and is brought closer to the other end portion. An unclamped state is established when the locked part locked by the locking part is unlocked by bending the other end portion such that the other end portion is displaced from the one end portion. The clamping device is configured to clamp the flexible tube in the clamped state where the first projection and the second projection are positioned close to each other and to intercept a flow of a fluid at a clamped position. The clamping device further includes a displacement-restricting member capable of restricting the displacement of the other end portion in a transition from the clamped state to the unclamped state.

According to the teachings herein, in the clamping device taught herein, the displacement-restricting member is a strap-like part that allows the displacement of the other end portion within a predetermined range but prevents the displacement of the other end portion beyond the predetermined range.

According to the teachings herein, the clamping device taught herein further includes an interfering part provided to the other end portion and being capable of preventing the movement of the locked part by interfering with the one end portion when the one end portion is further pressed with the locked part being locked by the locking part, and wall portions that are wall-like members standing from respective side edges of the other end portion toward the one end portion and being capable of preventing the flexible tube extending through the insertion hole from moving in a radial direction of the tube. Furthermore, the displacement-restricting member extends between the interfering part and the wall portions.

According to the teachings herein, in the clamping device taught herein, the displacement-restricting member is a standing part that allows the displacement of the other end portion within a predetermined range but prevents the displacement of the other end portion beyond the predetermined range.

According to the teachings herein, there is provided a medical circuit to which the clamping device according to the teachings herein are attached.

According to the teachings herein, the clamping device includes the displacement-restricting member capable of restricting the displacement of the other end portion in the transition from the clamped state to the unclamped state. Hence, excessive displacement of the other end portion in the transition from the clamped state to the unclamped state can be prevented.

According to the teachings herein, the displacement-restricting member is a strap-like part that allows the displacement of the other end portion within a predetermined range but prevents the displacement of the other end portion beyond the predetermined range. Hence, appropriate displacement of the other end portion in the transition from the clamped state to the unclamped state can be realized smoothly, and excessive displacement of the other end portion can be prevented.

According to the teachings herein, the clamping device includes the interfering part provided to the other end portion and being capable of preventing the movement of the locked part by interfering with the one end portion when the one end portion is further pressed with the locked part being locked by the locking part, and the wall portions that are wall-like members standing from the respective side edges of the other end portion toward the one end portion and being capable of preventing the flexible tube extending through the insertion hole from moving in the radial direction of the tube. Furthermore, the displacement-restricting member extends between the interfering part and the wall portions. Hence, while the function of the interfering part and the function of the wall portions are provided, the displacement-restricting member can also be provided by utilizing the interfering part and the wall portions.

According to the teachings herein, the displacement-restricting member is a standing part that allows the displacement of the other end portion within a predetermined range but prevents the displacement of the other end portion beyond the predetermined range. Hence, appropriate displacement of the other end portion in the transition from the clamped state to the unclamped state can be realized smoothly, and excessive displacement of the other end portion can be prevented.

According to the teachings herein, the medical circuit can exert the above advantageous effects exerted by the clamping device taught herein.

BRIEF DESCRIPTION OF THE DRAWINGS

FIG. 1 includes perspective views of a clamping device according to a first embodiment of the present teachings.

FIG. 2 is a side view of the clamping device (in an unclamped state).

FIG. 3 is another side view of the clamping device (in a clamped state).

FIG. 4 is yet another side view of the clamping device (with an interfering part interfering with an appropriate part).

FIG. 5 is yet another side view of the clamping device (with a displacement-restricting member preventing further displacement of an other end portion).

FIG. 6 is a schematic diagram of a medical circuit to which the clamping device is attached.

FIG. 7 includes perspective views of a clamping device according to a second embodiment of the present teachings.

FIG. 8 is a side view of the clamping device (in an unclamped state).

FIG. 9 is another side view of the clamping device (in a clamped state).

FIG. 10 is yet another side view of the clamping device (with an interfering part interfering with an appropriate part).

FIG. 11 is yet another side view of the clamping device (with a displacement-restricting member preventing further displacement of an other end portion).

DETAILED DESCRIPTION

Embodiments of the present teachings will now be described specifically with reference to the drawings.

A clamping device 1 according to a first embodiment clamps a flexible tube and thus intercepts the flow of a fluid at the clamped position. As illustrated in FIGS. 1 to 5, the clamping device 1 basically includes a one end portion 2 having a first projection 2a, an other end portion 3 having a second projection 3a, and a middle portion 4 continuous with the one end portion 2 and with the other end portion 3. These portions are integrally formed of a predetermined resin (preferably, but not limited to, a thermoplastic resin moldable by extrusion(injection) molding or the like: for example, polypropylene, polyethylene, polyacetal, or the like). The clamping device 1 illustrated in FIGS. 1 and 2 is in an unclamped state. The clamping device 1 illustrated in FIG. 3 is in a clamped state.

The one end portion 2 includes the first projection 2a integrally formed on the inner surface (a surface facing the other end portion 3) thereof in such a manner as to project downward. The outer surface of the one end portion 2 has irregularities for preventing fingers of the worker from slipping thereon during the clamping work. The one end portion 2 further includes a locked part 5 provided at the tip thereof and being lockable by a locking part 6 to be described later. The other end portion 3 includes the second projection 3a integrally formed thereon at a position facing the first projection 2a, and the locking part 6 integrally formed thereon and being capable of locking the locked part 5.

The middle portion 4 is a portion that is continuous with the one end portion 2 and with the other end portion 3 (a portion between the one end portion 2 and the other end portion 3) and has one insertion hole H1 into which a flexible tube T is to be inserted. Meanwhile, the other end portion 3 includes a part extending substantially linearly from the middle portion 4 (a part having the second projection 3a), and a part standing therefrom while being bent (a part having the locking part 6). The standing part has an other insertion hole H2 into which the flexible tube T is to be inserted.

When the clamping device 1 according to the first embodiment is in the unclamped state, as illustrated in FIG. 2, where the tip of the one end portion 2 and the tip of the other end portion 3 are spaced apart from each other, the flexible tube T is inserted into the one insertion hole H1 and into the other insertion hole H2. Then, the one end portion 2 is pressed in a direction ($\alpha$) indicated in FIG. 2, whereby the middle portion 4 is bent and the one end portion 2 is brought closer to the other end portion 3. Accordingly, as illustrated in FIG. 3, the locking part 6 locks the locked part 5, whereby the clamped state is established. In the clamped state, the first projection 2a and the second projection 3a are positioned close to each other and in combination clamp the flexible tube T extending through the insertion holes H1 and H2. Thus, the flow of the fluid can be intercepted at the clamped position.

In the clamped state illustrated in FIG. 3, when a tip part P2 of the other end portion 3 is pressed with a finger such that the other end portion 3 is bent in a direction ($\beta$) indicated in FIG. 3 and is thus displaced from the one end portion 2, the locked part 5 locked by the locking part 6 is unlocked, whereby the unclamped state illustrated in FIG. 2 can be established. That is, when the locked part 5 locked by the locking part 6 is unlocked, the tip of the one end portion 2 and the tip of the other end portion 3 spontaneously move away from each other under the restoring force exerted by the resin material forming the clamping device 1. In the unclamped state, the first projection 2a and the second projection 3a are spaced apart from each other, and the clamping of the flexible tube T is disabled (the unclamped state).

The clamping device 1 according to the first embodiment further includes wall portions 8 integrally formed on the other end portion 3 at two respective side edges of the other end portion 3. The wall portions 8 are wall-like members standing from the side edges of the other end portion 3 toward the one end portion 2 and can prevent the flexible tube T extending through the insertion holes H1 and H2 from moving in the radial direction of the flexible tube T (any directions orthogonal to the lengthwise direction). To avoid the interference of the one end portion 2 with the wall portions 8 in the clamped state, the one end portion 2 has cuts m at two respective side edges thereof.

The other end portion 3 according to the first embodiment further includes wall portions 10 integrally formed thereon at respective positions adjacent to the wall portions 8 (on a side thereof nearer to the middle portion 4). A recess L is provided between each of the wall portions 8 and a corresponding one of the wall portions 10. When the locked part 5 is locked by the locking part 6 and the flexible tube T is thus clamped as illustrated in FIG. 3, the two side ends of the first projection 2a go into the respective recesses L. That is, when the locked part 5 is locked by the locking part 6 and the two side ends of the first projection 2a are received by the respective recesses L, the first projection 2a and the second projection 3a can be positioned relative to each other in the lengthwise direction of the flexible tube T.

The other end portion 3 according to the first embodiment further includes interfering parts 7 integrally formed thereon. The interfering parts 7 are each a projection integrally provided on the inner side at the tip of the other end portion 3 and near the locking part 6. When the one end portion 2 is further pressed in the direction a with the locked part 5 being locked by the locking part 6 (in the clamped state illustrated in FIG. 3), the interfering parts 7 interfere with respective predetermined points P1 of the one end portion 2 as illustrated in FIG. 4. Thus, the further movement of the locked part 5 can be prevented. The points with which the interfering parts 7 according to the first embodiment interfere are the two side edges at the tip of the one end portion 2 and on the underside of the locked part 5.

The clamping device 1 according to the first embodiment includes displacement-restricting members 9 that are capable of restricting the displacement (displacement in the direction (β)) of the other end portion 3 that occurs in the transition from the clamped state to the unclamped state. As illustrated in FIG. 5, the displacement-restricting members 9 according to the first embodiment are each a strap-like part that allows the displacement of the other end portion 3 within a predetermined range but prevents the displacement of the other end portion 3 beyond the predetermined range. The displacement-restricting members 9 each extend from the underside of a corresponding one of the interfering parts 7 to a side part of a corresponding one of the wall portions 8. That is, if the other end portion 3 is displaced within the predetermined range, the displacement-restricting members 9 remain being in a bent state (a loose state). If it is attempted to displace the other end portion 3 beyond the predetermined range, the displacement-restricting members 9 are fully stretched as illustrated in FIG. 5, whereby further displacement is prevented.

As illustrated in FIG. 6, the clamping device 1 according to the first embodiment is attached to a blood circuit (a medical circuit) including an arterial blood circuit D1 and a venous blood circuit D2 for extracorporeally circulating the blood of a patient. Specifically, the clamping device 1 is connected to any of flow routes in the arterial blood circuit D1 and the venous blood circuit D2 and flow routes branching off therefrom and is capable of intercepting the flow of the blood that is under extracorporeal circulation, a physiological saline solution, or the like. In FIG. 6, the clamping device 1 is attached to each of a flow route branching off from the arterial blood circuit D1, and flow routes extending from a venous air-trap chamber (f) connected to the venous blood circuit D2. The clamping device may be attached to any position but to flexible tubes forming the medical circuit.

The arterial blood circuit D1 is provided at the distal end thereof with a shunt connector a to which an arterial puncture needle is attachable. The arterial blood circuit D1 is further provided with an arterial air-trap chamber (e) at a halfway point thereof and with a dialyzer connector (c) at the proximal end thereof. The dialyzer connector (c) is connectable to an arterial connector of a blood purifier (a dialyzer). The venous blood circuit D2 is provided at the distal end thereof with a shunt connector b to which a venous puncture needle is attachable. The venous blood circuit D2 is further provided with the venous air-trap chamber (f) at a halfway point thereof and with a dialyzer connector d at the proximal end thereof. The dialyzer connector (d) is connectable to a venous connector of the blood purifier (the dialyzer). Reference character B denotes a rubber button (a coinfusing member) that allows a drug or the like to be infused into the flexible tube or the blood or the like to be collected from the flexible tube.

The first embodiment employs the displacement-restricting members 9 that are capable of restricting the displacement of the other end portion 3 that occurs in the transition from the clamped state to the unclamped state. Hence, excessive displacement of the other end portion 3 in the transition from the clamped state to the unclamped state can be prevented. Accordingly, in the transition to the unclamped state, the other end portion 3 can be prevented from being excessively displaced and therefore being plastically deformed. Thus, the flexible tube T can be clamped again in a good and assured manner.

The displacement-restricting members 9 according to the first embodiment are each a strap-like part that allows the displacement of the other end portion 3 within a predetermined range but prevents the displacement of the other end portion 3 beyond the predetermined range. Hence, appropriate displacement of the other end portion 3 in the transition from the clamped state to the unclamped state can be realized smoothly, and excessive displacement of the other end portion 3 can be prevented. While the first embodiment concerns a case where the strap-like displacement-restricting members 9 are provided on the right and left sides, respectively, of the clamping device 1, a displacement-restricting member 9 may be provided only on one side of the clamping device 1.

The first embodiment further includes the interfering parts 7 provided on the other end portion 3 and that are capable of preventing the movement of the locked part 5 by interfering with the one end portion 2 when the one end portion 2 is further pressed with the locked part 5 being locked by the locking part 6, and the wall portions 8 that are wall-like members standing from the respective side edges of the other end portion 3 toward the one end portion 2 and are capable of preventing the flexible tube T extending through the insertion holes (H1 and H2) from moving in the radial direction of the flexible tube T. Furthermore, the displacement-restricting members 9 each extend between a corresponding one of the interfering parts 7 and a corresponding one of the wall portions 8. Hence, while the function of the interfering parts 7 and the function of the wall portions 8 are provided, the displacement-restricting members 9 can also be provided by utilizing the interfering parts 7 and the wall portions 8.

According to the first embodiment, the other end portion 3 includes the interfering parts 7. Moreover, when the one end portion 2 is further pressed in the direction (a) with the locked part 5 being locked by the locking part 6, the interfering parts 7 interfere with the respective predetermined points P1 of the one end portion 2, whereby the further movement of the locked part 5 can be prevented. That is, the locked part 5 can be prevented from interfering with any unintended parts other than the locking part 6 when the flexible tube T is clamped. Hence, the flexible tube T can be clamped in a good manner without fail, and the flow of the fluid in the flexible tube can be intercepted more exactly.

The interfering parts 7 according to the first embodiment are each a projection provided on the other end portion 3 near the locking part 6. When the one end portion 2 is further pressed in the direction a with the locked part 5 being locked by the locking part 6, the projection can interfere with a corresponding one of the predetermined points P1 of the one end portion 2. Hence, with the projections provided on the other end portion 3, the flexible tube T can be clamped in a good manner without fail, and the flow of the fluid in the flexible tube T can be intercepted more exactly. Furthermore, as illustrated in FIG. 6, if the clamping device 1 according to the first embodiment is attached to a medical circuit, the medical circuit can exert the above advantageous effects exerted by the clamping device 1.

Now, a clamping device according to a second embodiment of the present teachings will be described.

As with the case of the first embodiment, a clamping device 1 according to the second embodiment clamps a flexible tube and thus intercepts the flow of a fluid at the clamped position. As illustrated in FIGS. 7 to 11, the clamping device 1 basically includes the one end portion 2 having the first projection 2a, the other end portion 3 having the second projection 3a, and the middle portion 4 continuous with the one end portion 2 and with the other end portion 3. These portions are integrally formed of a predetermined resin (preferably, but not limited to, a thermoplastic resin moldable by extrusion (injection) molding or the like: for example, polypropylene, polyethylene, polyacetal, or the like). The clamping device 1 illustrated in FIGS. 7 and 8 is in the unclamped state. The clamping device 1 illustrated in FIG. 9 is in the clamped state. Elements that are the same as those employed in the first embodiment are denoted by respective ones of the corresponding reference numerals, and detailed description of such elements is omitted.

As with the case of the first embodiment, the clamping device 1 according to the second embodiment includes the interfering parts 7 integrally formed on the other end portion 3. The interfering parts 7 are each a projection integrally provided on the inner side at the tip of the other end portion 3 and near the locking part 6. When the one end portion 2 is further pressed in the direction a with the locked part 5 being locked by the locking part 6 (in the clamped state illustrated in FIG. 9), the interfering parts 7 interfere with respective predetermined points P1 of the one end portion 2 as illustrated in FIG. 10. Thus, the further movement of the locked part 5 can be prevented. As with the case of the first embodiment, the points with which the interfering parts 7 according to the first embodiment interfere are the two side edges at the tip of the one end portion 2 and on the underside of the locked part 5.

The clamping device 1 according to the second embodiment includes displacement-restricting members 9' that are capable of restricting the displacement (displacement in the direction (β)) of the other end portion 3 that occurs in the transition from the clamped state to the unclamped state. As illustrated in FIG. 11, the displacement-restricting members 9' according to the second embodiment are each a standing part that allows the displacement of the other end portion 3 within a predetermined range but prevents the displacement of the other end portion 3 beyond the predetermined range. The displacement-restricting members 9' are integrally formed on the other end portion 3. Specifically, if the other end portion 3 is displaced within the predetermined range, the other end portion 3 remains being spaced apart from the displacement-restricting members 9'. If it is attempted to displace the other end portion 3 beyond the predetermined range, the other end portion 3 interferes with the displacement-restricting members 9' as illustrated in FIG. 11, whereby further displacement is prevented.

The displacement-restricting members 9' according to the second embodiment are each a standing part that allows the displacement of the other end portion 3 within a predetermined range but prevents the displacement of the other end portion 3 beyond the predetermined range. Hence, appropriate displacement of the other end portion 3 in the transition from the clamped state to the unclamped state can be realized smoothly, and excessive displacement of the other end portion 3 can be prevented. Accordingly, in the transition to the unclamped state, the other end portion 3 can be prevented from being excessively displaced and therefore being plastically deformed. Thus, the flexible tube T can be clamped again in a good and assured manner.

While some embodiments have been described above, the present teachings are not limited thereto. For example, the other end portion 3 may include no interfering parts 7, no wall portions 8, or no recesses L that receive the first projection 2a. Moreover, the position, the shape, and the length of projection of the locking part 6 and the position, the shape, and other factors of the locked part 5 may be set arbitrarily. Furthermore, the position, the shape, and other factors of each displacement-restricting member may be set arbitrarily. The medical circuit to which the clamping device according to the present teachings are to be attached is not limited to a blood circuit and may be any of various medical circuits that include flexible tubes.

The present teachings are applicable to each of any clamping devices having different external shapes, any additional functions, and so forth, as long as the device includes a displacement-restricting member that is capable of restricting the displacement of the other end portion in the transition from the clamped state to the unclamped sate.

REFERENCE SIGN LIST 1 clamping device
2 one end portion
2a first projection
3 other end portion
3a second projection
4 middle portion
5 locked part
6 locking part
7 interfering part
8 wall portion
9, 9' displacement-restricting member
10 wall portion
T flexible tube
H1, H2 insertion hole

The invention claimed is:

1. A clamping device comprising:
a one end portion having a first projection on an inner side and a locked part at a tip;

an other end portion having a second projection at a position facing the first projection and a locking part capable of locking the locked part;

a middle portion continuous with the one end portion and with the other end portion;

an insertion hole allowing a flexible tube to be inserted between the first projection and the second projection;

an interfering part provided to the other end portion and being capable of preventing the movement of the locked part by interfering with the one end portion when the one end portion is further pressed with the locked part being locked by the locking part; and wall portions that are wall-like members standing from respective side edges of the other end portion toward the one end portion and being capable of preventing the flexible tube extending through the insertion hole from moving in a radial direction of the tube, wherein a clamped state where the locked part is locked by the locking part is established when the one end portion is pressed and is brought closer to the other end portion, and an unclamped state is established when the locked part locked by the locking part is unlocked by bending the other end portion such that the other end portion is displaced from the one end portion, the clamping device being configured to clamp the flexible tube in the clamped state where the first projection and the second projection are positioned close to each other and to intercept a flow of a fluid at a clamped position; and wherein the clamping device further includes a displacement-restricting member capable of restricting the displacement of the other end portion in a transition from the clamped state to the unclamped state, the displacement-restricting member being a strap-like part extending between the interfering part and the wall portions that allows the displacement of the other end portion within a predetermined range, but prevents the displacement of the other end portion beyond the predetermined range.

2. A medical circuit to which the clamping device according to claim 1 is attached.

3. The clamping device according to claim 1, wherein the displacement-restricting member extends from a single wall portion.

4. The clamping device according to claim 1, wherein the displacement-restricting member extends from opposing wall portions.

5. The clamping device according to claim 1, wherein the displacement-restricting member is a pair of displacement-restricting members, each displacement-restricting member extending from a wall portion.

* * * * *